| United States Patent [19] | [11] Patent Number: 4,661,474 |
| Umezawa et al. | [45] Date of Patent: Apr. 28, 1987 |

[54] 2′,3′-DIDEOXY-2′-FLUOROKANAMYCIN A AND 1-N-(α-HYDROXY-ω-AMINOALKANOYL) DERIVATIVES THEREOF

[75] Inventors: Hamao Umezawa; Sumio Umezawa, both of Tokyo; Tsutomu Tsuchiya, Yokohama; Yoshiaki Takahashi, Tokyo, all of Japan

[73] Assignee: Zaidan Hojin Biseibutsu Kagaku Kenkyu Kai, Tokyo, Japan

[21] Appl. No.: 807,485

[22] Filed: Dec. 10, 1985

[30] Foreign Application Priority Data

Dec. 15, 1984 [JP] Japan ................. 59-263759
Oct. 18, 1985 [JP] Japan ................. 60-231027

[51] Int. Cl.$^4$ ............... A61K 31/71; C07H 15/234
[52] U.S. Cl. ..................... 514/41; 536/13.7; 536/13.8; 536/17.9; 536/4.1; 536/18.7; 536/122; 536/55
[58] Field of Search .............. 536/13.7, 13.8; 514/41

[56] References Cited

U.S. PATENT DOCUMENTS

| 4,029,883 | 6/1977 | Hiraga et al. | 536/13.7 |
| 4,104,372 | 8/1978 | Umezawa et al. | 536/13.8 |
| 4,410,516 | 10/1983 | Umezawa et al. | 536/13.8 |
| 4,424,343 | 1/1984 | Cron et al. | 536/13.8 |

Primary Examiner—Johnnie R. Brown
Attorney, Agent, or Firm—Thomas P. Sarro

[57] ABSTRACT

New compounds, 2′,3′-dideoxy-2′-fluorokanamycin A and 1-N-(α-hydroxy-ω-aminoalkanoyl) derivatives thereof, particularly 1-N-(DL- or L-3-amino-2-hydroxypropionyl)- and 1-N-(L-4-amino-2-hydroxybutyryl)-2′,3′-dideoxy-2′-fluorokanamycins A are now provided, which are each useful as antibacterial agent. 2′,3′-Dideoxy-2′-fluorokanamycin A is prepared by a process comprising condensing a 6-azido-4-O-protected-2,3,6-trideoxy-2-fluoro-α-D-ribo-hexopyranosyl bromide with the 4-hydroxyl group of a 6-O-(2′,4′,6′-tri-O-protected-3′-N-protected-3′-amino-3′-deoxy-α-D-glucopyranosyl)-1,3-bis-N-protected-2-deoxystreptamine, reducing the resulting condensation product to convert its azido group into an amino group, and removing the remaining amino-protecting and hydroxyl-protecting groups from the reduction product.

6 Claims, No Drawings

2',3'-DIDEOXY-2'-FLUOROKANAMYCIN A AND 1-N-(α-HYDROXY-ω-AMINOALKANOYL) DERIVATIVES THEREOF

SUMMARY OF THE INVENTION

This invention relates to 2',3'-dideoxy-2'-fluorokanamycin A and 1-N-(α-hydroxy-ω-aminoalkanoyl) derivatives of 2',3'-dideoxy-2'-fluorokanamycin A which are new semisynthetic aminoglycosidic antibiotics and which are each a new compound exhibiting a high antibacterial activity against a variety of kanamycin-sensitive bacteria and kanamycin-resistant bacteria and are useful as antibacterial agent. This invention also relates to a pharmaceutical composition containing 2',3'-dideoxy-2'-fluorokanamycin A or a 1-N-(α-hydroxy-ω-aminoalkanoyl)-2',3'-dideoxy-2'-fluorokanamycin A as the active ingredient. This invention further relates to processes for the production of the new compounds of this invention.

BACKGROUND OF THE INVENTION

Various deoxy derivatives of kanamycins A, B and C as well as various 1-N-(α-hydroxy-ω-aminoalkanoyl) derivatives of the kanamycins A, B and C are already known as the semisynthetic aminoglycosidic antibiotics which are derived from the kanamycins. These known deoxy derivatives and 1-N-(α-hydroxy-ω-aminoalkanoyl) derivatives of the kanamycins have usefully high antibacterial activities, but the antibacterial spectra of these known derivatives of the kanamycins are of different ranges. Besides, these known kanamycin derivatives are possible to become inactive against such new resistant strains of bacteria which will possibly occur in future. Accordingly, it is always requested that new, antibacterial compounds having any more excellent properties than the known antibacterial kanamycin derivatives should be created and provided for use in therapeutic treatment of bacterial infections.

We, the present inventors, had an expectation that if we would succeed in synthetizing such a new kanamycin A derivative having the 3'-hydroxyl group replaced by a fluoro atom, namely a kanamycin A derivative identifiable as 3'-fluoro-3'-deoxykanamycin A, this new compound should be active against some kanamycin-resistant strains of bacteria which are already known and also against some another resistant strains which will possibly occur in future. With such expectation, we have made our efforts to synthetize 3'-fluoro-3'-deoxykanamycin A, and as a result of our researches we have succeeded in synthetizing 3'-fluoro-3'-deoxykanamycin A first time by a synthetic process wherein 3-deoxy-3-fluoro-1,2: 5,6-di-O-isopropylidene-α-D-glucofuranose, a known compound disclosed in the "Journal of Organic Chemistry" Vol. 43, No. 6, pages 1090–1092 (1978), is used as the starting compound and is subjected to a series of reaction steps, as described in the specification of Japanese patent application No. 161615/84 (filed Aug. 2, 1984); U.S. patent application Ser. No. 758,819, now U.S. Pat. No. 4,634,688; and European patent application No. 85 401575.7. We have also devised and provided a further process for the production of 3'-fluoro-3'-deoxykanamycin A which comprises starting from kanamycin A itself (Japanese patent application No. 261776/84, filed Dec. 13, 1984).

We have made our further research in an attempt to synthetize a new compound 3'-fluoro-3'-deoxykanamycin B and we have succeeded in synthetizing 3'-fluoro-3'-deoxykanamycin B according to a synthetic process wherein a known compound, 6'-N-, 4'-O-carbonyl-4'',6''-O-cyclohexylidene-1,2',3,3''-tetra-N-tosylkanamycin B which is disclosed as an N,O-protected kanamycin B derivative in Japanese patent application first publication "Kokai" No. 63993/81; U.S. Pat. No. 4,349,666; and the "Nippon Kagaku Kaishi" 1982, No. 10, pages 1706–1712 (1982) is employed as a starting compound (Japanese patent application No. 262700/84, filed Dec. 14, 1984). We have also succeeded in synthetizing new compounds, 1-N-(DL- or L-3-amino-2-hydroxy-propionyl)-3'-fluoro-3'-deoxykanamycins A and B, as well as 1-N-(L-4-amino-2-hydroxybutyryl)-3'-fluoro-3'-deoxykanamycins A and B by acylating the 1-amino group of the 3'-fluoro-3'-deoxykanamycin A or 3'-fluoro-3'-deoxykanamycin B as newly produced by us. We have further found that these new 1-N-(α-hydroxy-ω-aminoalkanoyl) derivatives of 3'-fluoro-3'-deoxykanamycins A and B are the new compounds having remarkable antibacterial activities against various gram-positive and gram-negative bacteria, including the resistant bacteria (Japanese patent application No. 76706/85, filed Apr. 12, 1985).

We have continued our researches and as a result, we have now succeeded in synthetizing a new compound, 2',3'-dideoxy-2'-fluorokanamycin A first time by a synthetic process in which a known compound methyl 4,6-O-benzylidene-3-deoxy-β-D-arabino-hexopyranoside disclosed in the "Can. J. Chem." Vol. 49, pages 796–799 (1971), and a known compound 6-O-(3'-amino-3'-deoxy-α-D-glucopyranosyl)-2-deoxystreptamine are used as the starting compounds and are reacted with each other according to a process as described and illustrated in Examples hereinafter. We have found that the new compound 2',3'-dideoxy-2'-fluorokanamycin A now synthetized exhibits an antibacterial activity against various gram-positive and gram-negative bacteria, including various kanamycin-resistant bacteria.

We have now also succeeded in synthetizing new compounds, 1-N-(DL- or L-3-amino-2-hydroxypropionyl)-2',3'-dideoxy-2'-fluorokanamycin A and 1-N-(L-4-amino-2-hydroxybutyryl)-2',3'-dideoxy-2'-fluorokanamycin A by acylating the 1-amino group of the 2',3'-dideoxy-2'-fluorokanamycin A with DL- or L-3-amino-2-hydroxypropionic acid or L-4-amino-2-hydroxybutyric acid. We have also found that these new 1-N-(α-hydroxy-ω-aminoalkanoyl) derivatives of 2',3'-dideoxy-2'-fluorokanamycin A have remarkable antibacterial activities against a variety of gram-positive bacteria and gram-negative bacteria, including various resistant bacteria. Based on these findings, we have accomplished this invention.

DETAILED DESCRIPTION OF THE INVENTION

According to a first aspect of this invention, therefore, there is provided a new compound represented by the formula

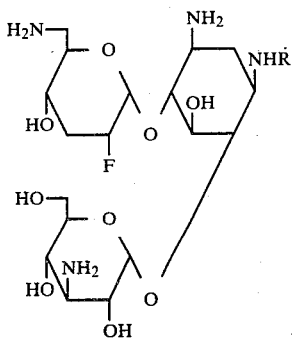

(I)

wherein R denotes a hydrogen atom or an α-hydroxy-ω-aminoalkanoyl group of the formula

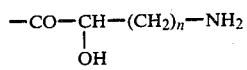

wherein n is an integer of 1 or 2, or a pharmaceutically acceptable acid addition salt of said new compound.

According to an embodiment of the first aspect of this invention, there are provided the new compound 2′,3′-dideoxy-2′-fluorokanamycin A of the formula

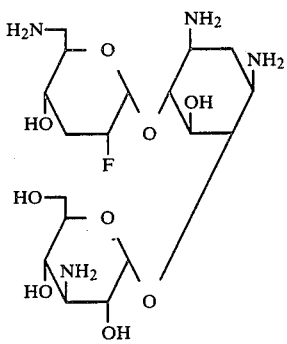

(Ia)

and a pharmaceutically acceptable acid addition salt thereof.

According to another embodiment of the first aspect of this invention, there are provided a 1-N-(α-hydroxy-ω-aminoalkanoyl)-2′,3′-dideoxy-2′-fluorokanamycin A of the formula

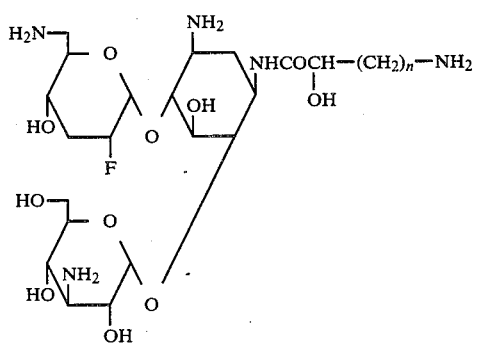

(Ib)

wherein n is an integer of 1 or 2, and a pharmaceutically acceptable acid addition salt thereof.

The new compound of the formula (Ib) according to this invention includes 1-N-(DL- or L-3-amino-2-hydroxypropionyl)-2′,3′-dideoxy-2′-fluorokanamycin A; and 1-N-(L-4-amino-2-hydroxybutyryl)-2′,3′-dideoxy-2′-fluorokanamycin A.

Thus, the new compound of the formula (I) according to this invention includes 2′,3′-dideoxy-2′-fluorokanamycin A; 1-N-(DL-3-amino-2-hydroxypropionyl)-2′,3′-dideoxy-2′-fluorokanamycin A; 1-N-(L-3-amino-2-hydroxypropionyl)-2′,3′-dideoxy-2′-fluorokanamycin A; and 1-N-(L-4-amino-2-hydroxybutyryl)-2′,3′-dideoxy-2′-fluorokanamycin A which are each a basic substance in the form of a colorless powder having no definite melting point and showing some physico-chemical properties as briefed in Examples 3-5 given hereinafter.

The new compound of the formula (I) according to this invention is usually obtained from the process of producing said new compound, in the form of a free base, a hydrate or a carbonate thereof. The new compound of the formula (I) may be converted into a pharmaceutically acceptable, non-toxic acid addition salt thereof in a known manner by reacting with a pharmaceutically acceptable inorganic acid such as hydrochloric acid, sulfuric acid, phosphoric acid, nitric acid and the like; or a pharmaceutically acceptable organic acid such as acetic acid, malic acid, citric acid, ascorbic acid methanesulfonic acid and the like.

According to a second aspect of this invention, there is provided an antibacterial composition comprising a compound of the formula (I) as above or a pharmaceutically acceptable acid addition salt thereof, as the active ingredient, in association with a pharmaceutically acceptable carrier for the active ingredient.

The minimum inhibitory concentrations (MIC., mcg/ml) of 1-N-(L-3-amino-2-hydroxypropionyl)-2′,3′-dideoxy-2′-fluorokanamycin A (abbreviated as 2′-F-isoseryl-DKMA); and 1-N-(L-4-amino-2-hydroxybutyryl)-2′,3′-dideoxy-2′-fluorokanamycin A (abbreviated as 2′-F-AHB-DKMA); and 2′,3′-dideoxy-2′-fluorokanamycin A (abbreviated as 2′-F-DKMA) according to this invention against various bacteria were determined by a standard serial dilution method, and the antibacterial spectra of these new compounds (each in the form of the free base) of this invention are shown in Table 1 below. For comparison, the antibacterial spectra of kanamycin A and amikacin, namely 1-N-(L-4-amino-2-hydroxybutyryl)-kanamycin A are also shown in Table 1.

TABLE 1

| | M.I.C. (mcg/ml) | | | | |
|---|---|---|---|---|---|
| Test organisms | 2'-F—isoseryl-DKMA | 2'-F—AHB—DKMA | 2'-F—DKMA | Amikacin (comparative) | Kanamycin A (comparative) |
| Staphylococcus aureus 209P | 0.78 | 0.78 | 3.12 | 1.56 | 1.56 |
| Staphylococcus aureus 209P Smith | 0.78 | 0.39 | 1.56 | 0.78 | 1.56 |
| Staphylococcus epidermidis 109 | 3.12 | 1.56 | 12.5 | 6.25 | |
| Bacillus anthracis | 0.39 | <0.2 | 1.56 | 0.39 | |
| Corynebacterium bovis 1810 | 0.78 | 0.78 | 12.5 | 1.56 | |
| Escherichia coli K-12 | 0.78 | 0.39 | 1.56 | 0.78 | 1.56 |
| Escherichia coli K-12 ML 1629 | 1.56 | 0.78 | 3.12 | 1.56 | >100 |
| Escherichia coli K-12 ML 1630 | — | — | 6.25 | — | >100 |
| Escherichia coli K-12 ML 1410R81 | 1.56 | 1.56 | 6.25 | 1.56 | >100 |
| Escherichia coli JR66/W677 | 3.12 | 1.56 | >100 | 3.12 | >100 |
| Mycobacterium 607 | 0.78 | 0.78 | 1.56 | 0.78 | 0.78 |
| Klebsiella pneumoniae 22 #3038 | 1.56 | 1.56 | 100 | 6.25 | |
| Proteus vulgaris OX 19 | 1.56 | 0.78 | 3.12 | 1.56 | |
| Serratia marcescens | 3.12 | 3.12 | 12.5 | 6.25 | |
| Providencia sp. Pv 16 | 1.56 | 0.78 | 6.25 | 1.56 | |
| Pseudomonas aeruginosa A3 | 0.2 | 0.39 | 0.78 | 0.2 | 25 |
| Pseudomonas aeruginosa H9 | 3.12 | 6.25 | 12.5 | 3.12 | |
| Pseudomonas aeruginosa No. 12 | | | 3.12 | | 25 |
| Pseudomonas aeruginosa H-11 | | | 25 | | 50 |
| Pseudomonas aeruginosa TI-13 | | | 12.5 | | 100 |
| Pseudomonas aeruginosa 99 | | | 25 | | >100 |

As will be clear from the antibacterial spectra of Table 1, 2',3'-dideoxy-2'-fluorokanamycin A of this invention exhibits a higher antibacterial activity than kanamycin A against various kanamycin-resistant bacteria, including the resistant strains of Escherichia coli and Pseudomonas aeruginosa. Besides, 1-N-(L-3-amino-2-hydroxypropionyl)-2',3'-dideoxy-2'-fluorokanamycin A and 1-N-(L-4-amino-2-hydroxybutyryl)-2',3'-dideoxy-2'-fluorokanamycin A of this invention exhibit high antibacterial activities against a wide range of the bacteria species, so that their antibacterial spectra are broad. It can also be seen that the 1-N-(α-hydroxy-ω-aminoalkanoyl) derivatives of 2',3'-dideoxy-2'-fluorokanamycin A exhibit enhanced antibacterial activities than the parent compound, 2',3'-dideoxy-2'-fluorokanamycin A. All the new compounds of the formula (I) according to this invention are of low acute toxicity, as shown by the fact that when 150 mg/kg of the new compound was given orally to mice, all the mice survived without showing any abnormal symptons.

The production of 2',3'-dideoxy-2'-fluorokanamycin A of the formula (Ia) according to this invention may be achieved by a process comprising three reaction stages, apart from the method which is required for the preparation of the starting compounds employed. Thus, a process for the production of 2',3'-dideoxy-2'-fluorokanamycin A may comprise a step (i) of reacting a 6-azido-4-O-protected-2,3,6-trideoxy-2-fluoro-α-D-ribo-hexopyranosyl bromide of the formula (II)

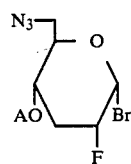
(II)

wherein A is a hydroxyl-protecting group such as an acyl group, preferably benzoyl group and an aralkyl group, preferably benzyl group, with the 4-hydroxyl group of a 6-O-(2',4',6'-tri-O-protected-3'-N-protected-3'-amino-3'-deoxy-α-D-glucopyranosyl)-1,3-bis-N-protected-2-deoxystreptamine of the formula (III)

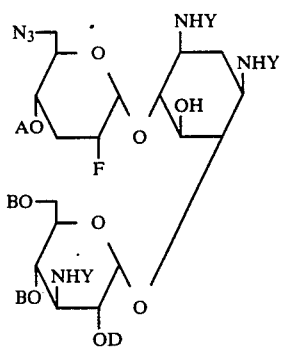
(III)

wherein Y is an amino-protecting group such as an alkoxycarbonyl group, an aralkyloxycarbonyl group, an alkylsulfonyl group, an arylsulfonyl group and an aralkylsulfonyl group; D is a hydroxyl-protecting group such as an acyl group; and every group B is a monovalent hydroxyl-protecting group, either same as or different from the group D and may be, for example, an acyl group or an aralkyl group, or a pair of two groups B as taken together form a di-valent hydroxyl-protecting group as selected from an alkylidene group, a cycloalkylidene group and an aralkylidene group, to produce a condensation product of the formula (IV)

(IV)

wherein A, B, D and Y are each as defined above; a step (ii) of reducing the azido group (—N₃) of the condensation product of the formula (IV) into an amino group (—NH$_2$), and a step (iii) of removing the remaining hydroxyl-protecting groups and amino-protecting groups (A, B, D, Y) from the amination product as obtained in the step (ii), thereby producing 2',3'-dideoxy-2'-fluorokanamycin A, namely the compound of the formula (Ia).

The starting compound of the formula (II) as above may be prepared by using such 6-azido-4-O-benzoyl-2,3,6-trideoxy-2-fluoro-α-D-ribo-hexopyranose as made by the method described in the Example 1, (a) to (d) given hereinafter, brominating the 1-hydroxyl group of said ribo-hexopyranose compound with thionyl bromide to produce 6-azido-4-O-benzoyl-2,3,6-trideoxy-2-fluoro-α-D-ribo-hexopyranosyl bromide (see the Example 1, (e) given hereinafter), and then, if desired, replacing the 4-O-benzoyl group of said ribo-hexopyranosyl bromide by another hydroxyl-protecting group (A) such as benzyl group.

The compound of the formula (III) to be reacted with the starting compound of the formula (II) may be prepared by protecting the 1-, 3- and 3'-amino groups of a known compound, 6-O-(3'-amino-3'-deoxy-α-D-glucopyranosyl)-2-deoxystreptamine with a known amino-protecting group (Y) such as tosyl group, and then protecting the 2'-hydroxyl group of the resulting 1,3,3'-tri-N-protected derivative of said known compound with a known hydroxyl-protecting group (D) such as acetyl group via three steps, to produce a 6-O-(2'-O-protected-3'-N-protected-3'-amino-3'-deoxy-α-D-glucopyranosyl)-1,3-bis-N-protected-2-deoxystreptamine (see the "Bulletin Chemical Society of Japan" Vol. 42, pages 533–537 (1969)), and further protecting the 4'- and 6'-hydroxyl groups of the latter deoxystreptamine compound with two mono-valent known hydroxyl-protecting groups (B), respectively, or with a di-valent known hydroxyl-protecting group, for example, an alkylidene group, preferably isopropylidene group, an aralkylidene group, preferably benzylidene group or a cycloalkylidene group, preferably a cyclohexylidene group (see the Example 2 given hereinafter).

In the method of preparing the compound of the formula (III), the sequence of the introduction of the amino-protecting groups and the hydroxyl-protecting groups may be changed and arranged conveniently, if necessary. Suitable examples of the compound of the formula (III) includes 6-O-(2'-O-acetyl-4',6'-O-cyclohexylidene-3'-deoxy-3'-tosylamino-α-D-glucopyranosyl)-1,3-bis-N-tosyl-2-deoxy-streptamine as prepared in the Example 2 given hereinafter; and 6-O-(2'-O-benzyl-3'-benzyloxycarbonylamino-4',6'-O-cyclohexylidene-3'-deoxy-α-D-glucopyranosyl)-1,3-bis-N-benzyloxycarbonyl-2-deoxystreptamine as prepared in the Example 2 of the aforesaid Japanese patent application No. 161615/84, U.S. patent application Ser. No. 758,819 or European patent application No. 85 401575.7.

In the process for the production of the 2',3'-dideoxy-2'-fluorokanamycin A of the formula (Ia) according to this invention, the step of reacting the compound of the formula (II) with the compound of the formula (III) by the condensation reaction may be carried out in the presence of mercuric cyanide as a condensation catalyst in an anhydrous organic solvent such as a chlorinated hydrocarbon, preferably dichloromethane at ambient temperature or at an elevated temperature, for example, at 10° C. to 100° C. under cooling or heating. The azido group (—N$_3$) of the condensation product of the formula (IV) so formed may be reduced into an amino group by a catalytic reduction with hydrogen in the presence of a palladium catalyst. The reduction of the azido group may be effected concurrently to the removal of the remaining amino-protecting groups, if desired. The step of removing the remaining hydroxyl-protecting groups and amino-protecting groups may be achieved in a known manner according to a conventional deprotection technique as properly chosen depending on the kinds of the protective groups to be cleaved and may optionally be effected in two or more separate stages. For instance, the reaction of the compound of the formula (II) with the compound of the formula (III) by the condensation, as well as the reduction of the azido group may be performed similarly to such procedures as illustrated in the specification of U.S. Pat. No. 3,929,761 in which a method for synthesis of 3'-deoxykanamycin A is described.

The reaction solution as obtained from the aforesaid step of removing the remaining protective groups may then be concentrated to dryness and the solid residue obtained may be taken up into a volume of water, followed by chromatographying the resultant aqueous solution containing the 2',3'-dideoxy-2'-fluorokanamycin A product in a column of a gel filtration agent, CM-Sephadex C-25 as developed with aqueous ammonia to effect the isolation and purification of the desired 2',3'-dideoxy-2'-fluorokanamycin A of the formula (Ia).

Generally speaking, the production of the 1-N-(α-hydroxy-ω-aminoalkanoyl)-2',3'-dideoxy-2'-fluorokanamycin A of formula (Ib) according to this invention may be achieved by acylating the 1-amino group of 2',3'-dideoxy-2'-fluorokanamycin A of the formula

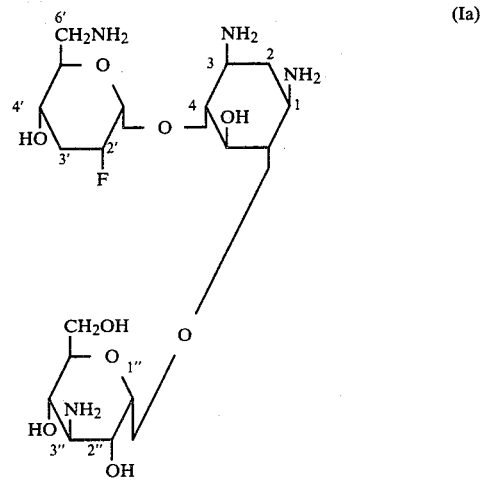

(Ia)

or such a partially N-protected 2',3'-dideoxy-2'-fluorokanamycin A derivative in which some or all of the three amino groups other than the 1-amino group each has been protected by a known amino-protecting group, with an α-hydroxy-ω-aminoalkanoic acid, particularly DL- or L-3-amino-2-hydroxypropionic acid or L-4-amino-2-hydroxybutyric acid, represented by the formula (V)

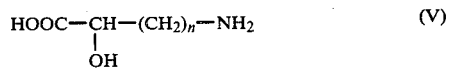

wherein n is an integer of 1 or 2. The α-hydroxy-ω-aminoalkanoic acid of the formula (V) as the acylating agent may also be in the form of its reactive acid derivative which reacts as a functional equivalent of the acid compound of the formula (V) and may be, for example, in the form of an active ester, an active azide, an active acid anhydride, a mixed acid anhydride or the like of the alkanoic acid compound (V). Besides, the amino group of the ω-amino-α-hydroxyalkanoic acid of formula (V) may preferably has been blocked with an amino-protecting group.

The 1-N-acylation of the starting 2',3'-dideoxy-2'-fluorokanamycin (Ia) with the acylating compound (V) may be carried out in a known manner. When either one or both of the starting compound (Ia) and the acylating agent compound of formula (V) employed has or have been N-protected, the resulting 1-N-acylated product is normally containing therein the amino groups which are remaining protected. Accordingly, it is then necessary to remove the remaining amino-protective groups from such 1-N-acylated product containing the protected amino groups, in order to afford the desired compound of formula (Ib).

According to a third aspect of this invention, therefore, there is provided a process for the production of 1-N-(α-hydroxy-ω-aminoalkanoyl)-2',3'-dideoxy-2'-fluorokanamycin A of formula (Ib), which comprises the steps of:

(i) acylating the 1-amino group of 2',3'-dideoxy-2'-fluorokanamycin A or a partially N-protected derivative thereof represented by the formula

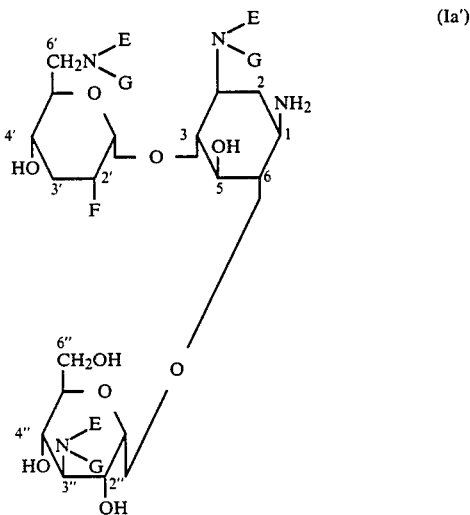

wherein E is a hydrogen atom and G is a hydrogen atom, or E is a hydrogen atom and at least one G is a mono-valent amino-protecting group but the other G(s) is or are each a hydrogen atom, or at least one pair of E and G taken together form a di-valent amino-protecting group but the other E and G are each a hydrogen atom, by reacting with an α-hydroxy-ω-aminoalkanoic acid or an amino-protected derivative thereof represented by the formula

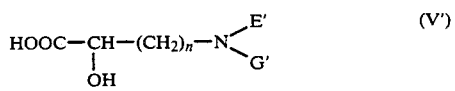

wherein E' is a hydrogen atom and G' is a hydrogen atom or a mono-valent amino-protecting group, or E' and G' taken together form a di-valent amino-protecting group and n is an integer of 1 or 2, or a reactive acid derivative thereof to produce the 1-N-acylated product represented by the formula

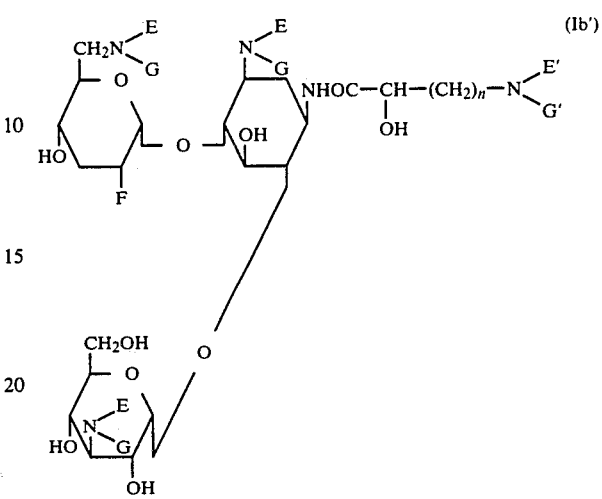

wherein E, G, E', G' and n are as defined above, and (ii) removing the remaining amino-protecting groups, where exist, from the 1-N-acylated product of formula (Ib') to produce the desired compound of formula (Ib).

In carrying out the process according to the third aspect of this invention, it is possible as the starting compound 2',3'-dideoxy-2'-fluorokanamycin A of formula (Ia) of which all the four amino groups are not protected, in the form of the free base or an acid addition salt thereof such as the hydrochloride or sulfate. However, it is preferred to employ as the starting compound such a partially N-protected derivative of 2',3'-dideoxy-2'-fluorokanamycin A in which all or some of the amino groups other than the 1-amino group have been protected with known amino-protecting groups and which may be prepared by introduction of the known amino-protecting groups into 2',3'-dideoxy-2'-fluorokanamycin A by means of a known amino-protection technique.

In general, an ordinary amino-protecting group may be used as the amino-protecting groups for the protection of some or all of the amino groups other than the 1-amino group of the starting 2',3'-dideoxy-2'-fluorokanamycin A of formula (Ia). The available amino-protecting groups include an alkyloxycarbonyl groups such as tert-butoxy-carbonyl and tert-amyloxycarbonyl; a cycloalkyloxycarbonyl group such as cyclohexyloxycarbonyl; an aralkyloxycarbonyl groups such as benzyloxycarbonyl; a hydrolytically cleavable, substituted lower alkanoyl group such as trifluoroacetyl and 0-nitrophenoxyacetyl; a phosphinothioyl group such as diphenylphosphinothioyl and dimethylphosphinothioyl; a phosphinyl group such as diphenylphosphinyl, and the like. Preferred examples of the di-valent amino-protecting group include phthaloyl group and a group of Shiff base type such as salicylidene. The introduction of the amino-protecting group of these kinds may be conducted by reacting the compound of formula (Ia) with an appropriate known reagent for introduction of the amino-protecting group which may be in the form of an acid halide, acid azide, active ester or acid anhydride and the like, in the manner known in the conventional synthesis of peptides. By chosing the quantity of the reagent for introduction of the amino-protecting group employed in a proportion of 0.5 to 6 mol per mol of the compound of formula (Ia), it is possible to prepare a mixture of different, partially amino-protected derivatives (Ia') at any ratio, due to the difference in the reactivity of the respective amino groups of the compound (Ia).

In the process of producing the new compound of the formula (Ib) according to this invention, it is feasible to employ, as the starting compound, such an amino-protected 2',3'-dideoxy-2'-fluorokanamycin A derivative in which all or some of the amino groups other than the 1-amino group have been protected, for example, a 3,6',3''-tri-N-protected derivative, a 3,6'-di-N-protected derivative, a 6',3''-di-N-protected derivative or a 6'-mono-N-protected derivative. Besides, a mixture of two or more of these partially N-protected derivatives may, without being purified or isolated, be used for the 1-N-acylation step of the present process.

In order to ensure that the desired compound of the general formula (Ib) can be produced in a high yield according to the process according to the third aspect of this invention, it needs only that just the 1-amino group of the starting compound of formula (Ia) is preferentially acylated with the α-hydroxy-ω-amino-alkanoic acid of formula (V'). Accordingly, it will be evident that most preferably, such a protected derivative of the compound (Ia) in which all the amino groups other than the 1-amino group have been protected, namely a 3,6',3''-tri-N-protected-2',3'-dideoxy-2'-fluorokanamycin A (Ia') is employed as the starting substance to be 1-N-acylated in the present process.

To prepare such a 3,6',3''-tri-N-protected-2',3'-dideoxy-2'-fluorokanamycin A derivative of formula (Ia') from the compound of formula (Ia), the following procedure may conveniently be used, for instance. Thus, a 3,6'-di-N-protected derivative of formula (Ia') is prepared at first from 2',3'-dideoxy-2'-fluorokanamycin A (Ia), either according to a known method of U.S. Pat. No. 4,136,254 (corresponding to Japanese patent application first publication "Kokai" No. 153944/77) comprising reacting 2',3'-dideoxy-2'-fluorokanamycin A with cation of a di-valent transition metal such as copper (II), nickel (II), cobalt (II) and others for the formation of a metal complex, reacting this metal complex with an acylation reagent known as the amino-protective group-introducing agent for the protective N-acylation of all the amino groups other than the 1- and 3''-amino groups of the kanamycin A moiety in the 2',3'-dideoxy-2'-fluorokanamycin A-metal complex [these 1- and 3''-amino groups having been blocked by complexing with the di-valent transition metal cation], and then removing the di-valent metal cation from the so protectively N-acylated 2',3'-dideoxy-2'-fluorokanamycin A-metal complex, e.g. by treatment with a cation-exchange resin or by treatment with hydrogen sulfide or aqueous ammonia to afford a 3,6'-di-N-acylated derivative of 2',3'-dideoxy-2'-fluorokanamycin A, or according to a method of claim 1 of our U.S. Pat. No. 4,297,485 (corresponding to our Japanese patent application first publication "Kokai" No. 64598/80; Japanese patent application No. 138402/78) comprising reacting 2',3'-dideoxy-2'-fluorokanamycin A with zinc cation in stead of the above-mentioned di-valent transition metal cation and subsequently processing the resultant zinc complex in a similar way to the above-mentioned known method of U.S. Pat. No. 4,136,254. In this way, a 3,6'-di-N-protected 2',3'-dideoxy-2'-fluorokanamycin A derivative of formula (Ia') can be prepared from the compound of formula (Ia) in a high yield. The 3''-amino group of this 3,6'-di-N-protected-2',3'-dideoxy-2'-fluorokanamycin A derivative so prepared can further be protected according to a selective 3''-N-acylation method of claim 15 of our U.S. Pat. No. 4,297,485 (also corresponding to Japanese patent application first publication "Kokai" No. 164696/80; Japanese patent application No. 73064/79) for the production of such an amino-protected derivative of an aminoglycoside antibiotic of which all the amino groups other than the 1-amino group have been protected selectively, so that a 3,6',3''-tri-N-protected derivative of the compound (Ia) can be prepared in a high yield. In accordance with the selective 3''-N-acylation method of the claim 15 of U.S. Pat. No. 4,297,485, the above-mentioned 3,6'-di-N-protected derivative of formula (T'a) is reacted with a formic acid alkyl ester, a di-halo- or tri-halo-alkanoic acid alkyl ester or N-formylimidazole as the acylation agent, whereby the 3''-amino group can be acylated selectively with the formyl or di- or tri-haloalkanoyl residue of said acylation agent in a high yield, without involving the acylation of the 1-amino group of said 3,6'-di-N-protected derivative. The 3,2',3''-tri-N-acylated derivative, for example, 3,6'-di-N-tert-butoxycarbonyl- or 3,6'-di-N-benzyloxycarbonyl-3''-N-trifluoroacetyl derivative of 2',3'-dideoxy-2'-fluorokanamycin A may be obtained by applying the above-mentioned method of the U.S. Pat. Nos. 4,136,254 and 4,297,485 and is a most preferred starting compound to be 1-N-acylated with the α-hydroxy-ω-amino-alkanoic acid (V') in the 1-N-acylation step of the present process.

In the process according to the third aspect of this invention, the 1-amino group of the compound of formula (Ia) or the 1-amino group of the partially amino-protected derivatives (Ia') thereof, either isolated or in mixture of two or more of them, is acylated with the α-hydroxy-ω-amino-alkanoic acid of formula (V') of which the amino group is either not protected or has been protected. This α-hydroxy-ω-amino-alkanoic acid may be DL- or L-3-amino-2-hydroxypropionic acid (i.e. the compound of formula (V') where n is 1; E' and G' are the hydrogen atoms) or L-4-amino-2-hydroxybutyric acid (i.e. the compound of formula (V') where n is 2; E' and G' are the hydrogen atoms). In the process according to the third aspect of this invention, the 1-n-acylation of the compound (Ia) or (Ia') with the α-hydroxy-ω-amino-alkanoic acid (V') may be conducted according to any of one conventional methods for the synthesis of peptides, for instance, according to the known dicyclohexylcarbodiimide method, the known mixed acid anhydride method, the known azide method or the active ester method and the like, using the α-hydroxy-ω-amino-alkanoic acid (V') as such or in the form of its reactive acid derivative (as a functional equivalent thereof). For the amino-protecting group for protection of the amino group of the α-hydroxy-ω-amino-alkanoic acid (V') may be employed such an amino-protecting group which is the same as or different from the one present in the starting compound (Ia'). Particularly, a preferred amino-protecting group for this purpose is tert-butoxycarbonyl group or p-methoxybenzyloxycarbonyl group which is easily cleavable by treatment with aqueous trifluoroacetic acid or acetic acid or with diluted aqueous hydrochloric acid. Benzyloxycarbonyl group which is removable by a conventional hydrogenolysis in the presence of a catalyst such as palladium or platinum oxide is also a convenient N-protecting group.

The 1-N-acylation of the starting compound (Ia) or (Ia') in the present process may desirably be carried out in an aqueous organic solvent according to the active ester method using the α-hydroxy-ω-amino-alkanoic acid compound (V') in the form of its active ester. For example, N-hydroxysuccinimide ester of L-4-tert-butoxycarbonylamino-2-hydroxybutyric acid may preferably be used as the active ester which may be prepared by a conventional method of preparing the active ester. This active ester may preferably be used in a proportion of from 1 to 3 molar equivalents and preferably of from 1 to 1.5 molar equivalents per mol of the starting compound (Ia) or (Ia') to be 1-N-acylated. The aqueous organic solvent used as the reaction medium may be a water-miscible organic solvent such as dioxane, 1,2-dimethoxyethane, dimethylformamide (DMF), tetrahydrofuran (THF), triethylamine and the like. The 1-N-acylation may be effected at ambient temperature but generally at a temperature of 0° C.-90° C., preferably of 0° C.-30° C. and for a reaction time of 10 minutes to 18 hours and preferably of 30 minutes to 60 minutes.

When the 1-N-acylation in the present process is conducted using as the starting compound such a partially amino-protected derivative (Ia') in which some, but not all, of the amino groups other than the 1-amino group has or have been protected, for example, the 6'-N-protected derivative of the starting compound (Ia'), the N-acylation products as formed may partially be purified by a column chromatography, for example, on silica gel so that the unreacted starting material is removed, giving a mixture of the desired 1-N-mono-acylated product with the otherwise N-acylated products. These mixed acylation products may, without being purified and/or isolated, be subjected immediately to the subsequent de-protecting step of the present process, followed by the step of purification and isolation so that the desired 1-N-mono-acylated product (Ib) is obtained.

In the second step of the process according to the third aspect of this invention, the 1-N-acylated product (including the mixed acylation products) as obtained from the 1-N-acylation step of the present process is subjected to the removal of the amino-protecting groups, if these are still remaining in the 1-N-acylated product. The removal of the protecting groups is effected by a conventional deprotecting technique. Thus, the amino-protecting group of the alkoxycarbonyl type is removed by acid hydrolysis with an aqueous solution of trifluoroacetic acid or acetic acid and the like or with a diluted aqeous solution of an inorganic acid such as hydrochloric acid. The aralkyloxycarbonyl group such as benzyloxycarbonyl may easily be removed by an ordinary catalytic reduction (hydrogenolysis). When phthaloyl group is remaining as the amino-protecting group, it can be removed by treating in a solution of hydrazine hydrate in a lower alkanol such as methanol.

It is convenient to conduct the synthesis of the new compound (Ib) of this invention according to such a particular multi-stage procedure as described below which is starting from 2',3'-dideoxy-2'-fluorokanamycin A and utilizing the selective N-protection methods of U.S. Pat. No. 4,297,485 (corresponding to Japanese patent application first publications "Kokai" No. 64598/80 and No. 164696/80).

Thus, according to this particular procedure, the starting 2',3'-dideoxy-2'-flurorokanamycin A (Compound a) and zinc acetate are either suspended in dimethylsulfoxide (DMSO) or dissolved in a mixture of water and dimethylformamide (DMF), and the resulting solution of the 2',3'-dideoxy-2'-fluorokanamycin A-zinc complex as formed is reacted with two or more molar proportion of N-benzyloxycarbonyloxy-succinimide

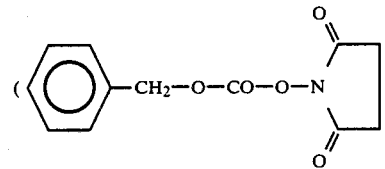

as an amino-protecting benzyloxycarbonyl group-introducing reagent) to protect the 3- and 6'-amino groups of the kanamycin A moiety of the zinc complex with the benzyloxycarbonyl groups, followed by removing the zinc cation from the resultant 3,6'-bis-N-benzyloxycarbonylated 2',3'-dideoxy-2'-fluorokanamycin A-zinc complex by treatment with a cation exchange resin such as Amberlite CG-50, to give 3,6'-bis-N-benzyloxycarbonyl-2',3'-dideoxy-2'-fluorokanamycin A (Compound b) (... Stage 1). Compound b is then reacted with ethyl trifluoroacetate in DMSO or DMF to protect the 3''-amino group of Compound b with the trifluoroacetyl group, affording 3,6'-bis-N-benzyloxycarbonyl-3''-N-trifluoroacetyl-2',3'-dideoxy-2'-fluorokanamycin A (Compound c) (... Stage 2). Further, Compound c is reacted with 4-N-benzyloxycarbonyl-L-4-amino-2-hydroxybutyric acid N-hydroxysuccinimide ester or with 3-N-benzyloxycarbonyl-L-3-amino-2-hydroxypropionic acid N-hydroxysuccinimide ester in aqueous tetrahydrofuran (THF) in the presence of sodium carbonate, so that the 1-amino group of Compound c is acylated with the 4-N-benzyloxycarbonyl-L-4-amino-2-hydroxybutyryl group or with the 3-N-benzyloxycarbonyl-L-3-amino-2-hydroxypropionyl group (... Stage 3), whereby there is formed 1-N-(N-benzyloxycarbonyl-L-4-amino-2-hydroxybutyryl)- or 1-N-(N-benzyloxycarbonyl-L-3-amino-2-hydroxypropionyl)-3,6'-bis-N-benzyloxycarbonyl-3''-N-trifluoroacetyl-2',3'-dideoxy-2'-fluorokanamycin A (Compound d) as the 1-N-acylation product.

Compound d is then subjected to the deprotecting treatment by acidic or alkaline hydrolysis for removal of the amino-protecting trifluoroacetyl group therefrom and subsequently by catalytic hydrogenolysis in the presence of a palladium catalyst for removal of the amino-protecting benzyloxycarbonyl groups therefrom (... Stage 4), so that the desired compound of formula (Ib) is afforded.

The antibacterial composition according to the aforesaid second aspect of this invention may be formulated into suitable forms for oral, parenteral or intrarectal administration. Composition in the form of injectable solution may contain 0.1% to 20.0% by weight of the compound (I) as active ingredient, and also one or more of a pH-adjuster, buffer, stabilizer, excipient, local anesthetics and an additive for rendering the solution isotonic. The injectable solution may be prepared to be adapted for subcutaneous, intramuscular or intravenous injection by any conventional pharmaceutical technique. Solid composition for oral administration which may be in the form of tablets, coated tablets, granules, powder and capsules, may contain excipients for the active ingredient, and if required, other additives, including disintegrators, lubricants, colorants, flavors and the like. The proportion of the active compound to the carrier may be at a ratio of 1:1 to 1:100 by weight and may usually be chosen appropriately depending on the form of the orally administrable formulation prepared. Suppository formulations may contain excipients and, if necessary, surfactant and lubricants additionally to the active compound.

The optimum dosage of the new compound (I) administered will, of course, depend on the mode of administration and the treatment aimed. For men, the unit dosage for injections generally contains from 50 mg to 200 mg of the compound (I), which may be administered intravenously or intramuscularly in divided doses one or more times per day. The new compound of the formula (I) used in the composition of this invention may be administered orally to an adult person at a dosage of 50 mg to 200 mg once a day.

This invention is now illustrated with reference to the following Examples 1 to 5. Example 1 shows the preparation of a starting compound of the formula (II), Example 2 shows the preparation of a reagent compound of the formula (III), and Examples 3 to 5 illustrates the production of the desired new compounds of the formulae (Ia) and (Ib) of this invention. In these Examples, Me denotes methyl group, Ph phenyl group, Bz benzoyl group, Ts tosyl group, Ac acetyl group, and Z benzyloxycarbonyl group, unless otherwise stated.

EXAMPLE 1

(a) Preparation of methyl 4,6-O-benzylidene-2,3-dideoxy-2-fluoro-β-D-ribo-hexopyranoside [Compound (2)] from methyl 4,6-O-benzylidene-3-deoxy-β-D-arabino-hexopyranoside [Compound (1)]

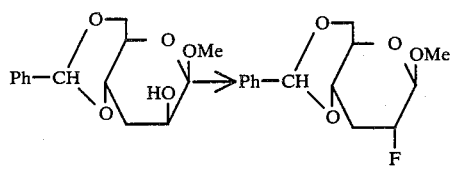

Compound (1)   Compound (2)

Diethylaminosulfur trifluoride (1.1 ml) was added to a mixture of dry benzene (25 ml) and dry pyridine (1.5 ml), and to the resulting mixture was added at 0° C. under stirring Compound (1) (500 mg) shown above which was a known compound [see E. H. Williams, W. A. Szarek and J. K. N. Jones: "Can. J. Chem.", 49, 796–799 (1971)] to give a solution. The stirring of the solution was continued at 0° C. for 0.5 hours and then at 60° C. for 3 hours. The reaction solution obtained was added to a saturated aqueous sodium hydrogen carbonate solution (250 ml) under ice-cooling, and the mixture was vigorously stirred for 0.5 hours and then extracted with benzene (100 ml). The benzene extract was washed with water, dried over anhydrous sodium sulfate and concentrated to give a syrup. This syrup was taken up into chloroform and the resultant solution was subjected to silica gel column chromatography (silica gel: 100 ml; eluent: chloroform) for purification, to give Compound (2) (391 mg) in the form of crystals. Yield: 78%.

(b) Preparation of methyl 4-O-benzoyl-6-bromo-2,3,6-trideoxy-2-fluoro-β-D-ribo-hexopyranoside [Compound (3)] from Compound (2)

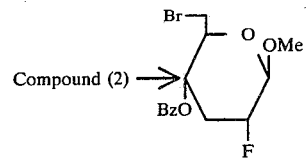

Compound (3)

A mixture of Compound (2) (391 mg) prepared in step (a) above, N-bromosuccinimide (285 mg) and barium carbonate (474 mg) in dry carbon tetrachloride (20 ml) was heated for 1 hour under reflux. The resulting suspension containing the reaction product was concentrated and the concentrate was extracted with chloroform. After the removal of insolubles by filtration, the chloroform-extract was washed with water, dried over anhydrous sodium sulfate and concentrated to give a crude product of Compound (3) (499 mg) as yellow crystals. Yield: 99%

(c) Preparation of methyl 6-azido-4-O-benzoyl-2,3,6-trideoxy-2-fluoro-β-D-ribo-hexopyranoside [Compound (4)] from Compound (3)

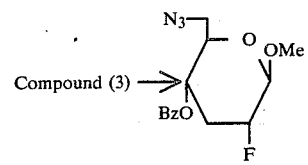

Compound (4)

The crude Compound (3) (499 mg) prepared in step (b) was dissolved in dry dimethylformamide (10 ml), to which was then added sodium azide (112 mg). The resulting mixture was heated at 100° C. for 0.5 hours to effect the reaction, after which the homogeneous reaction solution obtained was concentrated and then extracted with chloroform (100 ml). The extract was washed with water, dried over anhydrous sodium sulfate and concentrated to yield as yellowish brown syrup. This syrup was taken up in chloroform and the resulting solution was subjected to silica gel column chromatography (silica gel: 30 ml; eluent: chloroform) for purification to afford Compound (4) (430 mg) as a colourless syrup. Yield: 96% based on Compound (2).

(d) Preparation of 6-azido-4-O-benzoyl-2,3,6-trideoxy-2-fluoro-β-D-ribo-hexopyranose [Compound (5)] from Compound (4)

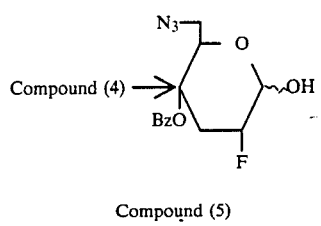

Compound (5)

Compound (4) (128 mg) prepared in step (c) above was dissolved in a mixture (2.6 ml) of trifluoroacetic acid-water (1:1) containing 6N hydrochloric acid. The reaction was conducted at 50° C. for 1 hour. The resulting reaction solution was diluted with water, neutralized with sodium hydrogen carbonate under ice-cooling and then extracted with chloroform. The extract was washed with water, dried over anhydrous sodium sulfate and concentrated to a syrup. This syrup was dissolved in ethyl acetate and purified by silica gel column chromatography (silica gel: 5 ml; eluent: toluene-ethyl acetate (6:1)) to give Compound (5) (110 mg) as a colurless syrup. Yield: 90%.

(e) Preparation of 6-azido-4-O-benzoyl-2,3,6-trideoxy-2-fluoro-α-D-ribo-hexopyranosyl bromide [Compound (6)] from Compound (5)

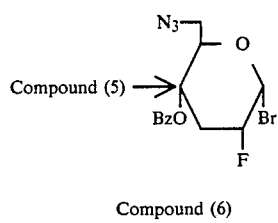

Compound (6)

Compound (5) (1.47 g) prepared in step (d) above was dissolved in dry dichloromethane (29 ml) and thionyl bromide (1.9 ml) was added to the solution. The reaction was conducted at room temperature for 36 hours. The resulting acidic reaction solution was neutralized with sodium hyrogen carbonate (80 g) and then extracted with dichloromethane. After the removal of insolubles by filtration, the extract was concentrated to a syrup, which was then dissolved in benzene and purified by silica gel column chromatograph (silica gel: 250 ml; eluent: benzene), yielding Compound (6) (1.03 ) as a colorless syrup. Yield: 58%.

Specific rotation: $[\alpha]_D^{21} + 186°$ (c 1, chloroform).
IR: 2110 cm$^{-1}$ (azido).
$^1$H-NMR spectrum (in deutero-chloroform with tetramethylsilane as internal standard): δ2.32 (1H, dddd,H-3ax), 2.64 (1H, m, H-3eq) 4.65 (1H, dddd, H-2), 5.14 (1H, dddd, H-4), 6.61 (1H, d, H-1) $^3J_{1,2}=3.8$, $^3J_{2,3ax}=12.0$, $^3J_{2,3eq}=4.7$, $^2J_{3ax,3eq}=12.0$, $^3J_{3ax,4}=12.0$, $^3J_{3eq,4}=5.0$, $^4J_{1,4}=\sim1$, $^3J_{1,F}=\sim0$, $^2J_{2,F}=47.5$, $^3J_{3ax,F}=8.3$, $^3J_{3eq,F}=5$. $^4J_{4,F}=1.5$ Hz

EXAMPLE 2

(a) Preparation of 6-O-(3'-deoxy-3'-tosylamino-α-D-glucopyranosyl)-1,3-bis-N-tosyl-2-deoxystreptamine [Compound (8)] from 6-O-(3'-amino-3'-deoxy-α-D-glucopyranosyl)-2-deoxystreptamine [Compound (7)]

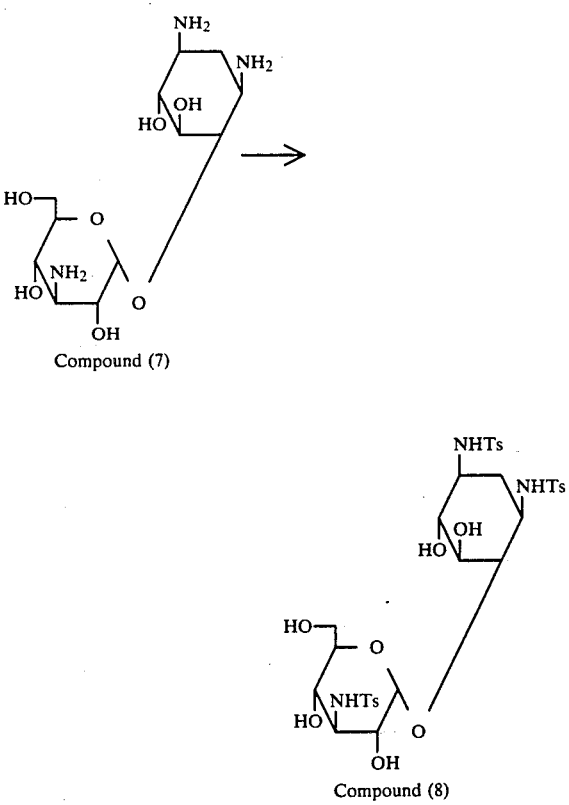

Compound (7) (15.0 g) which is a known compound and sodium carbonate (10.0 g) were dissolved in a mixture (300 ml) of dioxane-water(1:1), to which was then added tosyl chloride (27.7 g) under ice-cooling. The resultant mixture was stirred for 2 hours under ice-cooling and then at room temperature overnight (14 hours) to effect the N-tosylation reaction. The reaction solution was concentrated and the residue was extracted with ethyl acetate. The extract was washed with water, dried over anhydrous sodium sulfate and concentrated to afford Compound (8) (29.5 g) as a colorless solid. Yield: 81% based on Compound (7) (as free base).

(b) Preparation of 6-O-(4',6'-O-cyclohexylidene-3'-deoxy-3'-tosylamino-α-D-glucopyranosyl)-1,3-bis-N-tosyl-2-deoxystreptamine [Compound (9)] from Compound (8)

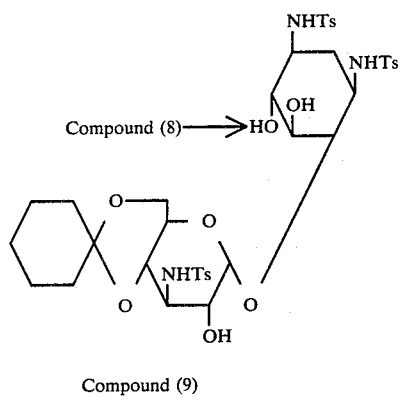

Compound (9)

Compound (8) (25.0 g) prepared in step (a) above was dissolved in dry N,N-dimethylformamide (300 ml). To this solution were added p-toluenesulfonic acid (1.1 g) and 1,1-dimethoxycyclohexane (5.3 ml), and the 4',6'-O-cyclohexylidenation reaction was conducted at 60° C., under a pressure of 20–25 mmHg for 1 hour.

The resulting reaction solution was added to a 5% aqueous sodium hydrogen carbonate solution (2 l) and the precipitate thus formed was recovered by filtration. The precipitated product so recovered was dissolved in chloroform-methanol (8:1) and the resultant solution was subjected to silica gel column chromatography (silica gel: 1.4 l; eluent: chloroform-methanol (8:1) for purification to give Compound (9) (16.1 g) as a colorless solid. Yield: 58%. At the same time, 4,5- and 4',6'-di-O-cyclohexylidenated homologue of compound (9) (5.7 g) was recovered. Yield: 19%.

(c) Preparation of 6-O-(2'-O-acetyl-4',6'-O-cyclohexylidene-3'-deoxy-3'-tosylamino-α-D-glucopyranosyl)-1,3-bis-N-tosyl-2-deoxystreptamine [Compound (10)] from Compound (9)

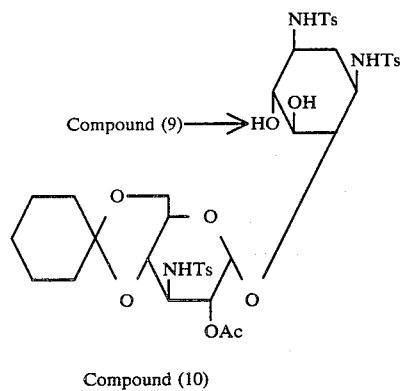

Compound (10)

Compound (9) (14.4 g) prepared in step (b) above was dissolved in a mixture (70 ml) of dry dimethylsulfoxide and dry pyridine (9:1), and to the resultant solution was added N-acetylimidazole (3.76 g). The resulting mixture was purged with nitrogen and the reaction for 2'-O-acetylation was conducted at room temperature for 27 hours.

The resulting reaction solution was added to a saturated aqueous solution (2 l) of sodium hydrogen carbonate, and the precipitate formed was removed, washed with water, then with ethyl ether and purified by subjecting the solution of it in chloroform-methanol (10:1) to silica gel column chromatography (silica gel: 1.2 l; eluent: chloroform-methanol (10:1)), yielding Compound (10) (10.1 g) as a colorless solid. Yield: 67%.

Specific rotation: $[\alpha]_D^{20} + 3°$ (c 1, chloroform). $[\alpha]_D^{20} + 68°$ (c 1, DMF).

$^1$H-NMR spectrum (in deutero-pyridine with tetramethylsilane as internal standard): δ2.23, 2.26, 2.28 (3H, s, CH$_3$—C$_6$H$_4$—SO$_2$—), 2.46 (3H,s, CH$_3$—CO—), 5.66 (1H, dd, H-2'), 6.24 (1H, d, H-1'), $^3J_{1',2'} = 3.8$ Hz, $^3J_{2',3'} = 10.5$ Hz.

EXAMPLE 3

(a) Preparation of 2''-O-acetyl-6'-azido-4'-O-benzoyl-4'',6''-O-cyclohexylidene-6'-deamino-2',3'-dideoxy-2'-fluoro-tris-N-tosylkanamycin A [Compound (11)]

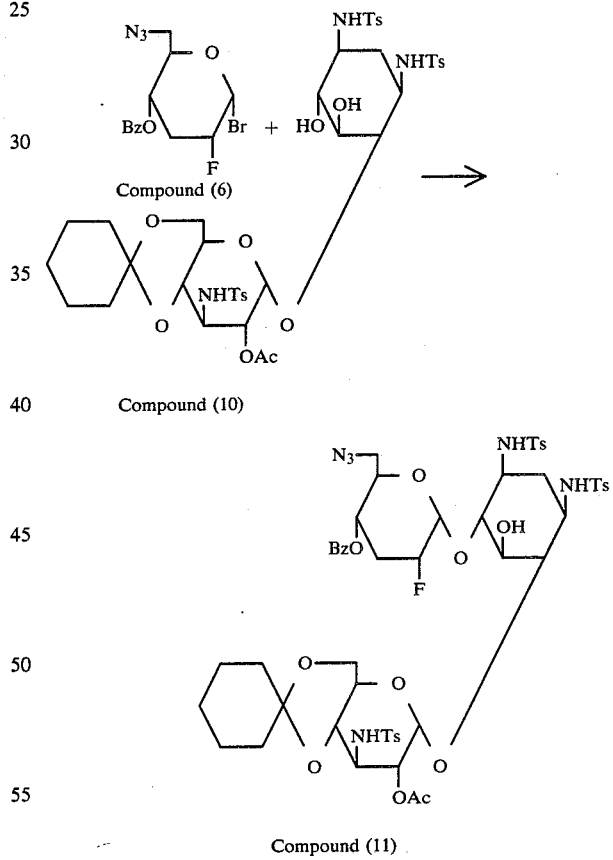

Compound (11)

Compound (6) (515 mg) prepared in Example 1 was dissolved in dry dichloromethane (1.3 ml), to which were then added pulverized "Drierite" (a calcium sulfate) (1.18 g) and pulverized mercuric cyanide (543 mg) and finally Compound (10) (638 mg) prepared in Example 2. The resulting solution was stirred at 40° C. for 7 hours in dark to effect the condensation reaction. The resultant suspension containing the reaction products thus formed was diluted with chloroform (100 ml) and then filtered with the aid of a filtration-did, Celite (a registered trade mark, sold by Johns Manville Sales Corp.). The filtrate was washed successively with a saturated aqueous sodium hydrogen carbonate solution and with water and then dried over anhydrous sodium sulfate and concentrated to yield a brown solid. This solid was dissolved in ethyl acetate and purified by silica gel column chromatography (silica gel: 130 ml; eluent; benzene-ethyl acetate (10:9)), affording a crude product of Compound (11) (300 mg) as pale yellow solid, together with the β-condensation product (225 mg). Yield: 27% based on Compound (10).

The crude Compound (11) (300 mg) was further purified by subjecting the solution of it in ethyl acetate again to silica gel column chromatography (silica gel: 60 ml; eluent: benzene-ethyl acetate (5:3)), yielding a pure product of the desired Compound (11) (134 mg) as a colorless solid.

Yield: 16% based on Compound (10).

(b) Preparation of 2',3'-dideoxy-2'-fluorokanamycin A [Compound Ia] from Compound (11)

Compound (11) (137 mg) as obtained in step (a) above was further purified by subjecting the solution of the compound in acetone to a Sephadex column chromatography [Sephadex LH-20: 17 ml; Sephadex is a registered trade mark, solid by Pharmacia; eluent: acetone]. Compound (11) (134.2 mg) in the form of a colorless solid so purified was dissolved in liquid ammonia (30 ml) at −50° C. Then, to the solution was added metallic sodium (200 mg), and the mixture obtained was stirred at −50° C. for 2 hours to involve the reduction of the azido group and the removal of the tosyl groups. Methanol (about 1 ml) was added to the reaction solution, when the color of the solution was changed from dark blue to pale yellow. The resultant solution was then concentrated to give a pale yellow residue, which was then dissolved in water (15 ml), when an alkaline hydrolysis occurred to remove the acetyl and benzoyl groups. The reaction mixture was neutralized with the addition of Amberlite CG-120 resin (H+ form, 200-400 mesh) (2.50 g) and filtered to recover the resin which was then washed with water and eluted with 1N aqueous ammonia. The eluate fractions positive to ninhydrin color reaction were collected and concentrated to yield a pale yellow solid. The solid was dissolved in a mixture (10 ml) of acetic acid-water (4:1) and the solution was heated at 80° C. for 0.5 hours to eliminate the cyclohexylidene group. The reaction solution was concentrated to dryness and the solid residue was dissolved in water. The solution was passed through a column of CM-Sephadex C-25 (20 ml), which was then eluted with aqueous ammonia with increasing concentrations from 0 to 0.15N. The fractions of eluate positive to ninhydrin coloration and containing the desired compound (75-95 ml) were combined together and concentrated to yield 2',3'-dideoxy-2'-fluorokanamycin A (14.1 mg) as a colorless solid. Yield 23% as a salt with $H_2CO_3$.

Specific rotation: $[\alpha]_D^{20} + 106°$ (c 0.5, water).

$^1$H-NMR (in 20% deutero-ammonia-deutero-water with tetramethylsilane as internal standard): δ 4.71 (1H, dddd, H-2'), 5.54 (1H, d, H-1'), $^3J_{1',2'} = 3.5$, $^3J_{1',F} = \sim 0$, $^2J_{2',F} = 48.0$ Hz.

EXAMPLE 4

(a) Preparation of 3,6'-bis-N-benzyloxycarbonyl-2',3'-dideoxy-2'-fluorokanamycin A [Compound (b)] from Compound (a) or of formula (Ia)

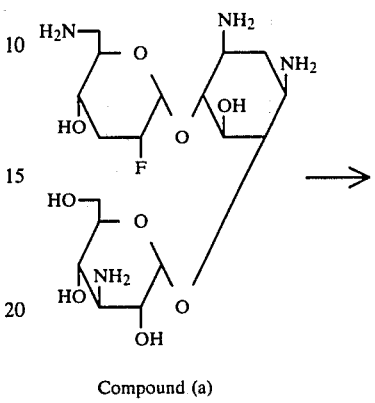

Compound (a)

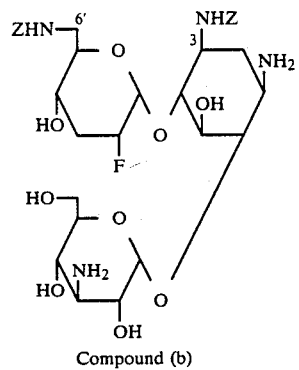

Compound (b)

2',3'-Dideoxy-2'-fluorokanamycin A [Compound (a) as above] in the form of a carbonate (48.9 mg) was suspended in dry dimethylsulfoxide (DMSO) (0.75 ml), and zinc acetate $Zn(OAc)_2.2H_2O$ (98 mg) was added to the resulting suspension. The resulting mixture was stirred at room temperature for 5 hours to give a homogeneous solution, to which N-(benzyloxycarbonyloxy)-succinimide (48 mg) was slowly added over 10 minutes under stirring. The stirring was continued at room temperature for further 1 hour to complete the reaction of protecting the amino groups with the benzyloxycarbonyl group.

The reaction solution was washed with ethyl ether repeatedly and the resulting syrup was passed through a column of Amberlite CG-50 resin (a mixture of the H+ form and the $NH_4^+$ form at 1:1 ratio by volume) (10 ml). The resin of the column was washed with a mixture of tetrahydrofuran-water (1:1) and eluted with a mixture of tetrahydrofuran-water (1:1) containing 0.5N ammonia. Eluate fractions containing the desired compound were combined together and concentrated at 25° C. in vacuo to a volume of 3 ml. The concentrate was diluted with water and neutralized with carbon dioxide as blown thereinto several times, followed by concentrating to dryness to yield the titled Compound (b) (49.4 mg) as a colorless solid.

(b) Preparation of 3,6'-bis-N-benzyloxycarbonyl-2',3'-dideoxy-2'-fluoro-3''-N-trifluoroacetylkanamycin A [Compound (c)] from Compound (b)

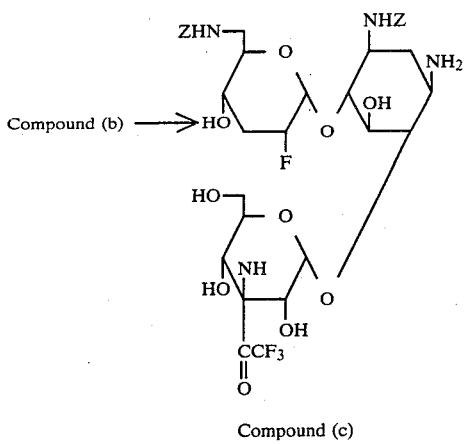

Compound (c)

Compound (b) (49.0 mg) which was obtained in step (a) above was dissolved in dry dimethylsulfoxide (0.2 ml). To the solution was added a solution (0.1 ml) of ethyl trifluoroacetate (0.0095 ml) in dry dimethylsulfoxide and the mixture was stirred at room temperature for 30 minutes to conduct the 3''-N-trifluoroacetylation for the amino-protecting purpose.

Addition of ethyl ether to the resulting reaction solution gave a colorless syrup which was then washed with a further amount of ethyl ether, affording a colorless solid (64.4 mg). The solid so obtained was dissolved in methanol (1 ml), and ethyl ether was added to the methanol solution to deposit a precipitate which was then washed with a further amount of ethyl ether yielding Compound (c) (50.0 mg) as a colorless solid.

(c) Preparation of 3,6'-bis-N-benzyloxycarbonyl-1-N-(L-4-benzyloxycarbonylamino-2-hydroxybutyryl)-2',3'-dideoxy-2'-fluoro-3''-N-trifluoroacetylkanamycin A [Compound (d-1)] from Compound (c)

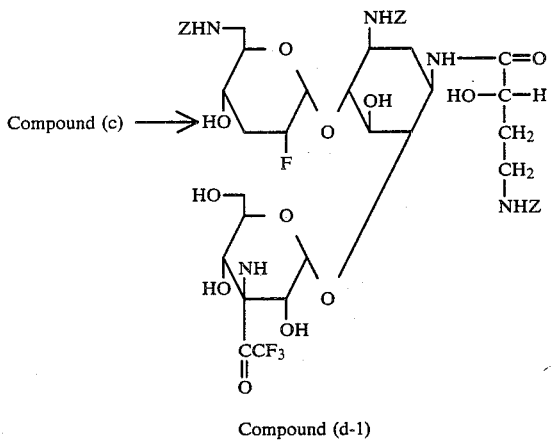

Compound (d-1)

Compound (c) (50 mg) obtained in step (b) above and sodium carbonate (8.0 mg) were dissolved in a mixture (1.3 ml) of tetrahydrofuran and water (1:1). To the resulting solution was added a solution of N-hydroxysuccinimide ester of L-4-benzyloxycarbonylamino-2-hydroxybutyric acid (30 mg) in tetrahydrofuran (0.7 ml). The reaction was conducted at room temperature for 10 minutes for the 1-N-acylation. The reaction solution was then concentrated and the residue was washed with water. The residue was dissolved in the developing solvent as described next and purified by silica gel column chromatography [silica gel: 7 ml; the developing solvent used was comprising: the lower layer of the mixture of chloroform-methanol-water (4:3:2)], affording Compound (d-1) (46.9 mg) as a colorless solid.

(d) Preparation of 1-N-(L-4-amino-2-hydroxybutyryl)-2',3'-dideoxy-2'-fluorokanamycin A [Compound (Ib-1)] from Compound (d-1)

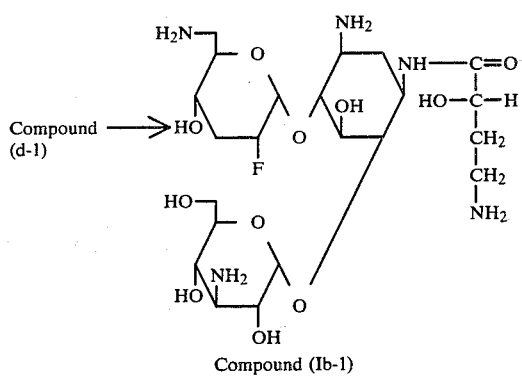

Compound (Ib-1)

Compound (d-1) (46.0 mg) obtained in step (c) above was dissolved in a mixture (2 ml) of 2N aqueous ammonia-tetrahydrofuran (1:1). The resultant mixture was subjected to hydrolysis at room temperture overnight (for 15 hours) to remove the 3''-N-trifluoroacetyl group. The reaction solution obtained was concentrated to dryness and the solid residue was dissolved in a mixture (4.2 ml) of acetic acid-dioxane-water (1:10:10). Catalytic reduction for eliminating the N-benzyloxycarbonyl groups was effected by passing hydrogen gas through the resulting solution at room temperature for 1 hour in the presence of palladium black as catalyst. The reaction mixture was filtered and the filtrate was concentrated to dryness. The residue was dissolved in water and passed through a column of CM-Sephadex C-25 (10 ml). Elution was effected with aqueous ammonia with increasing concentrations from 0 to 0.5N. The eluate fractions positive to ninhydrin coloration and containing the desired compound (40–60 ml) was combined together and concentrated to yield the titled Compound (Ib-1) (22.2 mg) as a colorless solid.

Specific rotation: $[\alpha]_D^{24} +77°$ (c 1, water).

$^1$H-NMR Spectrum (250 MHz, in 20% deutero-ammonia-deutero-water, with tetramethylsilane as internal standard): δ 4.16 (1H dd, H-2'''), 4.72 (1H, ddt, H-2'), 5.52 (1H d, H-1').

EXAMPLE 5

(a) Preparation of 3,6'-bis-N-benzyloxycarbonyl-1-N-(L-3-benzyloxycarbonylamino-2-hydroxypropionyl)-2',3'-dideoxy-2'-fluoro-3''-N-trifluoroacetylkanamycin A [Compound (d-2)] from Compound (c)

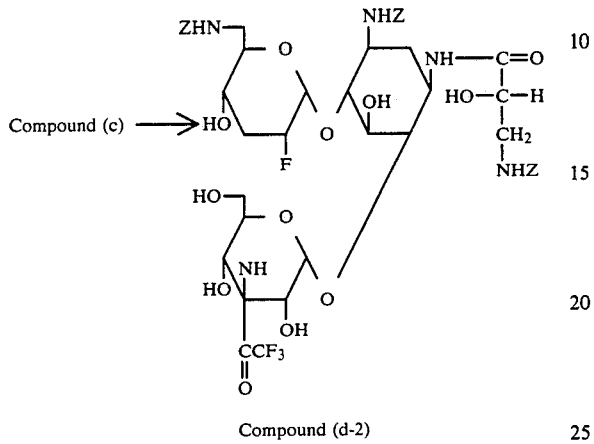

Compound (d-2)

A solution in tetrahydrofuran (0.5 ml) of N-hydroxysuccinimide ester (25 mg) of L-3-benzyloxycarbonylamino-2-hydroxypropionic acid which was prepared from N-benzyloxycarbonyl-L-isoserine and N-hydroxysuccinimide was added to a solution of Compound (c) (47 mg) as obtained in step (b) of Example 4 and sodium carbonate (6.0 mg) which were dissolved in a mixture (1 ml) of tetrahydrofuran and water (1:1). The resulting reaction mixture was stirred at room temperature for 20 minutes to conduct the 1-N-acylation reaction intended. The resulting reaction solution was concentrated and the solid residue was washed with water and then dissolved in the lower layer of chloroform-methanol-water (4:3:2), followed by silica gel column chromatography [silica gel: 6 ml; eluent: the lower layer of chloroform-methanol-water (4:3:2)] for purification, to afford Compound (d-2) (43.8 mg) as a colorless solid.

(b) Preparation of 1-N-(L-3-amino-2-hydroxypropionyl)-2',3'-dideoxy-2'-fluorokanamycin A [Compound (Ib-2) from Compound (d-2)

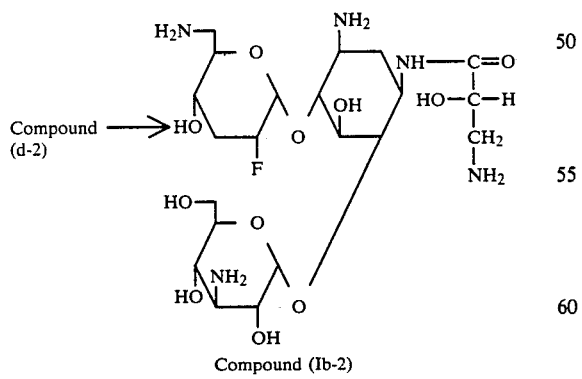

Compound (Ib-2)

Compound (d-2) (43.0 mg) obtained in step (a) above was dissolved in a mixture (2 ml) of 2N aqueous ammonia-tetrahydrofuran (1:1), and the solution was stirred at room temperature overnight (for about 18 hours) to conduct the reaction for the removal of 3''-N-trifluoroacetyl group. Then, the reaction solution was concentrated to dryness and the resulting solid residue was dissolved in a mixture (2.1 ml) of acetic acid-dioxane-water (1:10:10). The solution obtained was catalytically reduced by blowing hydrogen therein at room temperature for 1 hour in the presence of palladium black as catalyst to eliminate the N-benzyloxycarbonyl groups. The reaction mixture was filtered and the filtrate was concentrated to dryness. The solid residue was dissolved in water and the solution was passed through a column of 8 ml of CM-Sephadex C-25. Then, the column was washed with water and eluted with 0→0.5N aqueous ammonia. Eluate fractions containing to the desired product were collected and concentrated to dryness, affording the titled Compound (Ib-2) (21.3 mg).

Specific rotation: $[\alpha]_D^{24} + 80°$ (c 1, water).

What we claim is:

1. A compound represented by the formula

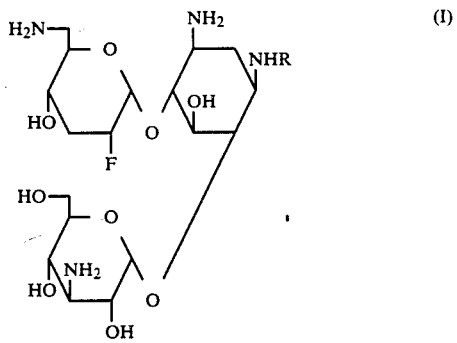

(I)

wherein R denotes a hydrogen atom or an α-hydroxy-ω-aminoalkanoyl group of the formula

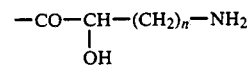

wherein n is an integer of 1 or 2, or a pharmaceutically acceptable acid addition salt of said compound.

2. A compound as claimed in claim 1, which is 2',3'-dideoxy-2'-fluorokanamycin A or a pharmaceutically acceptable acid addition salt thereof.

3. A compound represented by the formula

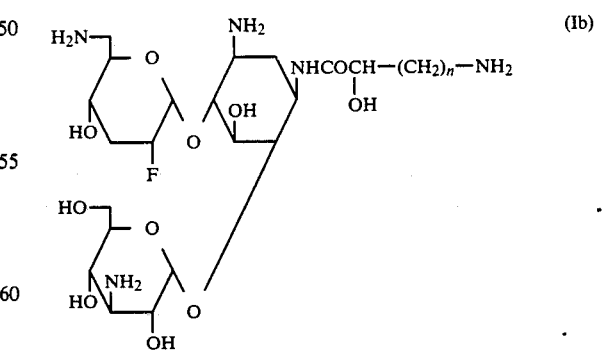

(Ib)

wherein n is an integer of 1 or 2, and a pharmaceutically acceptable acid addition salt thereof.

4. A compound which is 1-N-(DL- or L-3-amino-2-hydroxypropionyl)-2',3'-dideoxy-2'-fluorokanamycin A or a pharmaceutically acceptable acid addition salt.

5. A compound which is 1-N-(L-4-amino-2-hydroxybutyryl)-2',3'-dideoxy-2'-fluorokanamycin A or a pharmaceutically acceptable acid addition salt thereof.

6. An antibacterial composition comprising an antibacterially effective amount of a compound of the formula (I) as defined in claim 1 or a pharmaceutically acceptable acid addition salt thereof as the active ingredient, in combination with a carrier for the active ingredient.

* * * * *